US009023345B2

(12) United States Patent
Knight et al.

(10) Patent No.: US 9,023,345 B2
(45) Date of Patent: May 5, 2015

(54) METHODS FOR IMPROVING GUT HEALTH

(75) Inventors: Chris D. Knight, St. Charles, MO (US);
Julia J. Dibner, St. Charles, MO (US);
Fenglan Yan, St. Charles, MO (US)

(73) Assignee: Novus International, Inc., St. Charles, MO (US)

( * ) Notice: Subject to any disclaimer, the term of this patent is extended or adjusted under 35 U.S.C. 154(b) by 522 days.

(21) Appl. No.: 13/079,541

(22) Filed: Apr. 4, 2011

(65) Prior Publication Data

US 2012/0225050 A1 Sep. 6, 2012

Related U.S. Application Data

(60) Provisional application No. 61/447,861, filed on Mar. 1, 2011.

(51) Int. Cl.
| | |
|---|---|
| A61K 38/48 | (2006.01) |
| A23K 1/16 | (2006.01) |
| A23K 1/165 | (2006.01) |
| A23K 1/18 | (2006.01) |
| A23K 1/00 | (2006.01) |

(52) U.S. Cl.
CPC ............... *A61K 38/48* (2013.01); *A23K 1/1631* (2013.01); *A23K 1/1653* (2013.01); *A23K 1/1813* (2013.01); *A23K 1/1826* (2013.01); *A23K 1/184* (2013.01); *A23K 1/007* (2013.01); *A61K 38/482* (2013.01); *A61K 38/4873* (2013.01); *A61K 38/488* (2013.01); *A61K 38/4886* (2013.01); *C12Y 304/00* (2013.01); *C12Y 304/21* (2013.01); *C12Y 304/22* (2013.01); *C12Y 304/23* (2013.01); *C12Y 304/24* (2013.01)

(58) Field of Classification Search
None
See application file for complete search history.

(56) References Cited

U.S. PATENT DOCUMENTS

| | | | | |
|---|---|---|---|---|
| 2004/0052895 | A1* | 3/2004 | Ivey et al. | 426/2 |
| 2004/0101525 | A1* | 5/2004 | Lin et al. | 424/115 |
| 2007/0202088 | A1* | 8/2007 | Baltzley et al. | 424/93.46 |

OTHER PUBLICATIONS

Mantsala et al., "Extracellular and Membrane-Bound Proteases from *Bacillus subtilis*," Journal of Bacteriology, vol. 141, No. 2, pp. 493-501 (1980).*
Strongin et al., "Intracellular Serine Protease of *Bacillus subtilis*: Sequence Homology with Extracellular Subtilisins," Journal of Bacteriology, vol. 133, No. 3, pp. 1401-1411 (1978).*
Mantsala et al., "Extracellular and Membrane-Bound Proteases from *Bacillus subtilis*," Journal of Bacteriology, vol. 141, No. 2, pp. 493-501 (1980) (of record).*
Strongin et al., "Intracellular Serine Protease of *Bacillus subtilis*: Sequence Homology with Extracellular Subtilisins," Journal of Bacteriology, vol. 133, No. 3, pp. 1401-1411 (1978) (of record).*
Awad et al. (Poultry Science, vol. 88, No. 1, pp. 49-56; 2009).*
Timmerman et al. (Poultry Science, vol. 85, No. 8, pp. 1383-1388; 2006).*
Allen et al., "Recent Advances in Biology and Immunobiology of *Eimeria*Species and in Diagnosis and Control of Infection with These Coccidian Parasites of Poultry", Clinical Microbiology Review, 2002, pp. 58-65, Vol. 15, No. 1.
Bedford et al., "Reduction of Intestinal Viscosity through Manipulation of Dietary Rye and Pentosanase Concentration is Effected through Changes in the Carbohydrate Composition of the Intestinal Aqueous Phase and Results in Improved Growth Rate and Food Conversion Efficiency of Broiler Chicks", The Journal of Nutrition, 1992, pp. 560-569, vol. 122.
Choct et al., "Effects of xylanase supplementation on between-bird variation in energy metabolism and the number of *Clostridium perfringens* in broilers fed a wheat-based diet", Australian Journal of Agricultural Research, 2006, pp. 1017-1021, vol. 57, No. 9.
Collier et al., "Effects of Tylosin on Bacterial Mucolysis, *Clostridium perfringens* Colonization, and Intestinal Barrier Function in a Chick Model of Necrotic Enteritis", Antimicrobial Agents and Chemotherapy, 2003, pp. 3311-3317, vol. 47, No. 10.
Dibner et al., "Mechanisms of Intestinal Barrier Failure in Subclinical Enteritis", 58th Western Poultry Disease Conference, Sacramento, CA, Mar. 23-25, 2009, pp. 26-28.
Hoerr, "Pathogenesis of Enteric Diseases" Poultry Science, 1998, pp. 1150-1155, vol. 77.
McQuaid et al., "Physiological Society Symposium: Impaired endothelial and Smooth Muscle Cell Function in Oxidative Stress; Endothelial Barrier Dysfunction and Oxidative Stress: Roles for Nitric Oxide", Experimental Physiology, 1997, pp. 369-376, vol. 82.
Prescott et al., "The use of Bacitracin in the Prevention and Treatment of Experimentally-induced Necrotic Enteritis in the Chicken", The Canadian Veterinary Journal, 1978, pp. 181-183, vol. 19.
Teirlynck et al., "The cereal type in feed influences gut wall morphology and intestinal immune cell infiltration in broiler chickens", British Journal of Nutrition, 2009, pp. 1453-1461, vol. 102.
Truscott et al., "Reproduction and treatment of necrotic enteritis in broilers", American Journal of Veterinary Research, 1977, pp. 857-861, vol. 38, No. 6.
Unno et al., "Inhibition of inducible nitric oxide synthase ameliorates endotoxin-induced gut mucosal barrier dysfunction in rats", Gastroenterology, 1997, pp. 1246-1257, vol. 113, No. 4.
Wilson et al. "Manifestations of *Clostridium perfringens* and related bacterial enterides in broiler chickens", World's Poultry Science Journal, 2005, pp. 435-449, vol. 61, Issue 3.
Chiba, "Diet Formulation & Common Feed Ingredients," Animal Nutrition Handbook, Section 18, 2009, pp. 481-531.
Roush et al., "Optimization of Phase Feeding of Starter, Grower, and Finisher Diets for Male Broilers by Mixture Experimental Design: Forty-Eight-Day Production Period," Poultry Science, 2004, pp. 1264-1275, vol. 83.
Walker et al., "Types of Swine Diets," University of Florida, Cooperative Extension Service, Institute of Food and Agricultural Sciences, AS 44, Apr. 1989, pp. 1-3.

* cited by examiner

*Primary Examiner* — Cherie M Stanfield
*Assistant Examiner* — Paul D. Pyla
(74) *Attorney, Agent, or Firm* — Polsinelli PC

(57) ABSTRACT

The present invention provides methods for improving gut health. In particular, the invention provides methods for improving gut health by improving the digestibility of dietary proteins, decreasing the flow of protein to the lower gastrointestinal tract, and/or decreasing the levels of *Clostridium* bacteria the upper intestinal tract of a subject. The methods comprise administering to the subject a supplement consisting essentially of at least one protease.

2 Claims, 8 Drawing Sheets

METHODS FOR IMPROVING GUT HEALTH

CROSS-REFERENCE TO RELATED APPLICATION

This application claims priority to U.S. Provisional Application Ser. No. 61/447,861 filed on Mar. 1, 2011, which is hereby incorporated by reference in its entirety.

FIELD OF THE INVENTION

The present invention generally relates to methods for promoting or improving gut health. In particular, the invention relates to methods for reducing the levels of *Clostridium* bacteria in the upper gastrointestinal tract of a subject.

BACKGROUND OF THE INVENTION

The gastrointestinal tract not only is involved in digestion and absorption, but also interacts with the immune system to promote good health. The inside of the intestinal tract is coated with a thin layer of sticky, viscous mucous, and embedded in this mucus layer, are millions and millions of bacteria and other microbes. When the intestinal bacteria are in balance (i.e., the good bacteria outnumber the bad bacteria), the gut is said to be healthy. Intestinal problems arise, however, when the levels of pathogenic bacteria increase or when bacteria that normally populate the lower intestinal tract are relocated to the upper intestinal tract. Because of the relationship between good gut health and the overall health and well being of the organism, means for promoting or improving gut health are needed. For example, there is a need for methods for improving gut health by improving the digestibility of dietary proteins and/or decreasing the levels of bacteria comprising *Clostridium* in the upper intestinal tract of an organism.

SUMMARY OF THE INVENTION

Among the various aspects of the present invention is the provision of a method for decreasing a population of bacteria comprising a *Clostridium* species in the upper gastrointestinal tract of a subject. The method comprises administering to the subject a supplement consisting essentially of at least one protease in combination with a diet comprising a protein source that is digestible in the upper gastrointestinal tract and fermentable in the lower gastrointestinal tract of the subject, wherein the population of bacteria comprising the *Clostridium* species is reduced the upper gastrointestinal tract of the subject.

Another aspect of the invention encompasses a method for reducing protein flow to the lower intestinal tract of a subject. The method comprises administering to the subject a supplement consisting essentially of at least one protease in combination with a diet comprising a protein source that is digestible in the upper gastrointestinal tract and fermentable in the lower gastrointestinal tract of the subject, wherein reduction of protein flow to the lower intestinal tract decreases a population of bacteria comprising a *Clostridium* species in the upper gastrointestinal tract of the subject.

Other features and iterations of the invention are described in more detail below.

DETAILED DESCRIPTION OF THE INVENTION

Figure 1:
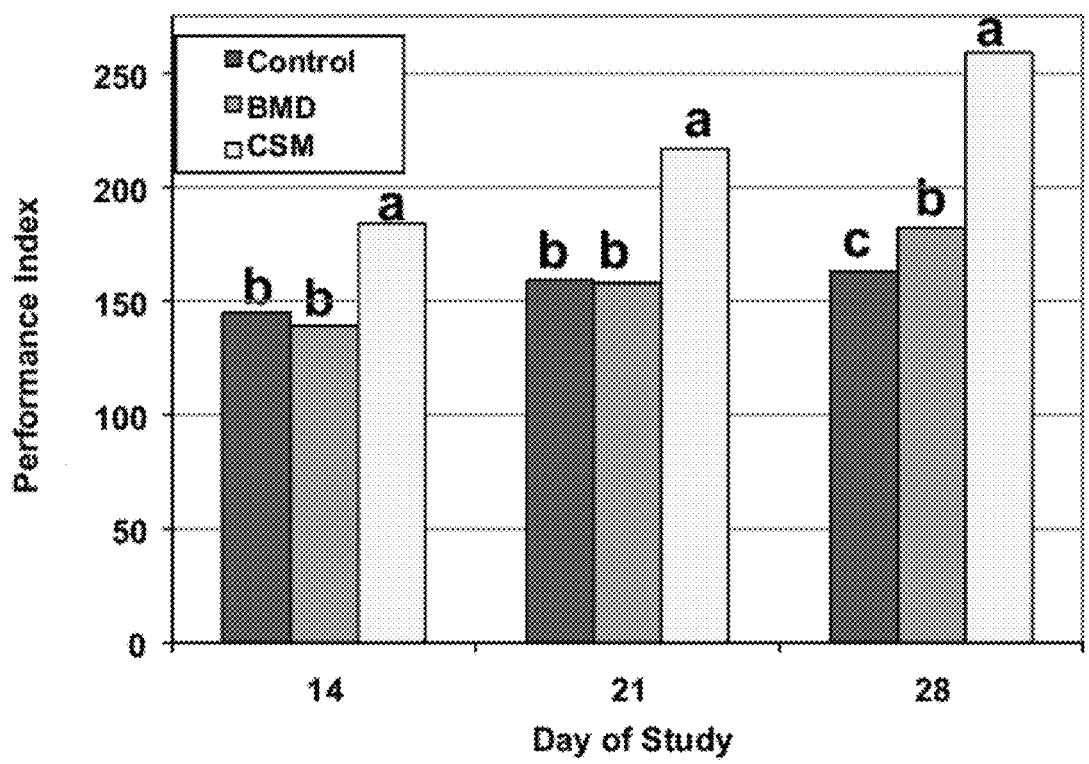
FIG. 1 illustrates that supplementation with NSP enzymes improved the performance index irrespective of coccidiosis challenge. Plotted is the period performance index (i.e., period gain×livability)/period feed efficiency) for each group at days 7, 21, and 28. Broilers were fed a rye-wheat diet. Treatment groups were: no additive (control), antibiotic (DMP), and NSP enzymes (CSM) (a,b,c; $P<0.01$).

Among the various aspects of the present invention, therefore, is the provision of a supplement and methods for improving gut health in a subject. The supplement for improving gut health consists essentially of at least one protease. The methods for improving gut health comprise administering to the subject the supplement, wherein gut health is improved by increasing the digestibility of dietary proteins, reducing the flow of undigested protein to the lower gastrointestinal tract, and decreasing the level of bacteria comprising *Clostridium* in the upper gastrointestinal tract of the subject.

(I) Supplement

One aspect of the present disclosure provides a supplement consisting essentially of a protease or a combination of proteases. A protease is a proteolytic enzyme that cleaves peptide bonds between adjacent amino acid residues in a protein (or peptide) substrate. Since a protease digests a protein into smaller and smaller amino acid chains, the supplement containing the protease(s) may improve the digestibility of dietary proteins.

As used herein, the terms "digestibility of dietary protein" or "protein digestibility" refers to the efficiency of absorption of the ingested protein, i.e., the amount of ingested protein that is absorbed by the body. Digestion in the stomach and the proximal small intestine breaks down the ingested protein into smaller amino acid units. Typically, single amino acids, dipeptides, and tripeptides can be absorbed by intestinal cells, in which further digestion takes place such that individual amino acids are absorbed into the blood stream. The dietary protein that is not digested into small enough units to be absorbed by upper intestinal cells is passed on through the rest of the gastrointestinal tract. No dietary protein has a digestibility of 100%. Rather the digestibility of various protein sources may range widely. For example, some proteins may be virtually undigestible and other proteins may be highly digestible (e.g., egg and dairy proteins are about 97% digestible in humans). The supplement consisting essentially of the protease(s), therefore, may improve the digestibility of a dietary protein.

Since the supplement consists essentially of at least one protease, the supplement is devoid of other enzymes such as, e.g., starch hydrolyzing carbohydrases, non-starch hydrolyzing carbohydrases, lipases, and nucleases. The supplement also is devoid of a quaternary ammonium carboxylate inner salt (e.g., betaine or related compounds). Non-protease enzymes and/or quaternary ammonium carboxylate inner salts do not affect the digestibility of dietary proteins.

(a) Protease

The identity of the protease (also known as peptidase or proteinase) in the supplement may vary. The protease may be an endoprotease or an exoprotease. In various embodiments, the protease may be an aspartic protease, an asparagine protease, a cysteine protease, a glutamic protease, a metalloprotease, a serine protease, a threonine protease, a protease of unknown catalytic function, or combinations thereof.

In one embodiment, the protease may be an aspartic (A) protease/peptidase chosen from pepsin A (*Homo sapiens*), nepenthesin (*Nepenthes gracilis*), HIV-1 retropepsin (human immunodeficiency virus 1), Ty3 transposon peptidase (*Saccharomyces cerevisiae*), Gypsy transposon peptidase (*Drosophila melanogaster*), Osvaldo retrotransposon peptidase (*Drosophila buzzatii*), retrotransposon peptidase (*Schizosaccharomyces pombe*), retrotransposon 17.6 peptidase (*Drosophila melanogaster*), walleye dermal sarcoma virus retropepsin (walleye dermal sarcoma virus), cauliflower mosaic virus-type peptidase (cauliflower mosaic virus), bacilliform virus peptidase (rice tungro bacilliform virus), thermopsin (*Sulfolobus acidocaldarius*), signal peptidase II (*Escherichia coli*), spumapepsin (human spumaretrovirus), Copia transposon peptidase (*Drosophila melanogaster*), Ty1 transposon peptidase (*Saccharomyces cerevisiae*), presenilin 1 (*Homo sapiens*), impas 1 peptidase (*Homo sapiens*), type 4 prepilin peptidase 1 (*Pseudomonas aeruginosa*), preflagellin peptidase (*Methanococcus maripaludis*), gpr peptidase (*Bacillus megaterium*), omptin (*Escherichia coli*), HybD peptidase (*Escherichia coli*), and skin aspartic protease (*Mus musculus*).

In another embodiment, the protease may be a cysteine (C) protease/peptidases chosen from papain (*Carica papaya*), bleomycin hydrolase (*Saccharomyces cerevisiae*), calpain-2 (*Homo sapiens*), Tpr peptidase (*Porphyromonas gingivalis*), poliovirus-type picornain 3C (human poliovirus 1), enterovirus picornain 2A (human poliovirus 1), foot-and-mouth disease virus picornain 3C (foot-and-mouth disease virus), cowpea mosaic comovirus-type picornain 3C (cowpea mosaic virus), hepatitis A virus-type picornain 3C (hepatitis A virus), parechovirus picornain 3C (human parechovirus 1), rice tungro spherical virus-type peptidase (rice tungro spherical virus), nuclear-inclusion-a peptidase (plum pox virus), adenain (human adenovirus type 2), potato virus Y-type helper component peptidase (potato virus Y), chestnut blight fungus virus p29 peptidase (*Cryphonectria hypovirus*), chestnut blight fungus virus p48 peptidase (*Cryphonectria hypovirus* 1, sindbis virus-type nsP2 peptidase (Sindbis virus), streptopain (*Streptococcus pyogenes*), clostripain (*Clostridium histolyticum*), ubiquitinyl hydrolase-L1 (*Homo sapiens*), legumain (*Canavalia ensiformis*), caspase-1 (*Rattus norvegicus*), metacaspase Yca1 (*Saccharomyces cerevisiae*), pyroglutamyl-peptidase I (*Bacillus amyloliquefaciens*), murine hepatitis coronavirus papain-like peptidase 1 (murine hepatitis virus), murine hepatitis coronavirus papain-like peptidase 2 (murine hepatitis virus), hepatitis C virus peptidase 2 (hepatitis C virus), ubiquitin-specific peptidase 14 (*Homo sapiens*), tymovirus peptidase (turnip yellow mosaic virus), carlavirus peptidase (apple stem pitting virus), rabbit hemorrhagic disease virus 3C-like peptidase (rabbit hemorrhagic disease virus), gingipain R (*Porphyromonas gingivalis*), gamma-glutamyl hydrolase (*Rattus norvegicus*), rubella virus peptidase (Rubella virus), foot-and-mouth disease virus L-peptidase (foot-and-mouth disease virus), porcine transmissible gastroenteritis virus-type main peptidase (transmissible gastroenteritis virus), porcine reproductive and respiratory syndrome arterivirus-type cysteine peptidase alpha (lactate-dehydrogenase-elevating virus), equine arteritis virus-type cysteine peptidase (porcine reproductive and respiratory syndrome virus), equine arteritis virus Nsp2-type cysteine peptidase (equine arteritis virus), beet necrotic yellow vein furovirus-type papain-like peptidase (beet necrotic yellow vein virus), calicivirin (Southampton virus), bacteriocin-processing peptidase (*Pediococcus acidilactici*), dipeptidyl-peptidase VI (*Bacillus sphaericus*), beet yellows virus-type papain-like peptidase (beet yellows virus), amidophosphoribosyltransferase precursor (*Homo sapiens*), acyl-coenzyme A:6-aminopenicillanic acid acyl-transferase precursor (*Penicillium chrysogenum*), hedgehog protein (*Drosophila melanogaster*), staphopain A (*Staphylococcus aureus*), Ulp1 peptidase (*Saccharomyces cerevisiae*), separase (*Saccharomyces cerevisiae*), D-alanyl-glycyl peptidase (*Staphylococcus aureus*), pestivirus Npro peptidase (classical swine fever virus), autophagin-1 (*Homo sapiens*), YopJ peptidase (*Yersinia pseudotuberculosis*), PfpI peptidase (*Pyrococcus furiosus*), vaccinia virus I7L processing peptidase (vaccinia virus), YopT peptidase (*Yersinia pestis*), HopN1 peptidase (*Pseudomonas syringae*), penicillin V acylase precursor (*Bacillus sphaericus*), sortase A (*Staphylococcus aureus*), sortase B (*Staphylococcus aureus*), gill-associated virus 3C-like peptidase (gill-associated virus), African swine fever virus processing peptidase (African swine fever virus), Cezanne deubiquitinylating peptidase (*Homo sapiens*), otubain-1 (*Homo sapiens*), IdeS peptidase (*Streptococcus pyogenes*), CylD protein (*Homo sapiens*), dipeptidase A (*Lactobacillus helveticus*), AvrRpt2 peptidase (*Pseudomonas syringae*), pseudomurein endoisopeptidase Pei (*Methanobacterium* phage psiM2), pestivirus NS2 peptidase (bovine viral diarrhea virus 1), AgrB peptidase (*Staphylococcus aureus*), UL36 deubiquitinylating peptidase (human herpesvirus 1), UfSP1 peptidase (*Mus musculus*), ElaD peptidase (*Escherichia coli*), RTX self-cleaving toxin (*Vibrio chol-* erae), L,D-transpeptidase (*Enterococcus faecium*), gamma-glutamylcysteine dipeptidyltranspeptidase (*Nostoc* sp. PCC 7120), prtH peptidase (*Bacteroides forsythus*), DUBA deubiquitinylating enzyme (*Homo sapiens*), ataxin-3 (*Homo sapiens*), nairovirus deuquitinylating peptidase (Crimean-Congo hemorrhagic fever virus), OTU1 peptidase (*Saccharomyces cerevisiae*), and acid ceramidase precursor (*Homo sapiens*).

In still another embodiment, the protease may be a glutamic (G) protease/peptidases such as scytalidoglutamic peptidase (*Scytalidium lignicolum*).

In a further embodiment, the protease may be a metallo (M) protease/peptidases chosen from aminopeptidase N (*Homo sapiens*), angiotensin-converting enzyme peptidase unit 1 (*Homo sapiens*), thimet oligopeptidase (*Rattus norvegicus*), oligopeptidase F (*Lactococcus lactis*), thermolysin (*Bacillus thermoproteolyticus*), mycolysin (*Streptomyces cacaoi*), immune inhibitor A (*Bacillus thuringiensis*), snapalysin (*Streptomyces lividans*), leishmanolysin (*Leishmania major*), bacterial collagenase V (*Vibrio alginolyticus*), bacterial collagenase H (*Clostridium histolyticum*), matrix metallopeptidase-1 (*Homo sapiens*), serralysin (*Serratia marcescens*), fragilysin (*Bacteroides fragilis*), gametolysin (*Chlamydomonas reinhardtii*), astacin (*Astacus astacus*), adamalysin (*Crotalus adamanteus*), neprilysin (*Homo sapiens*), carboxypeptidase A1 (*Homo sapiens*), carboxypeptidase E (*Bos taurus*), gamma-D-glutamyl-meso-diaminopimelate peptidase I (*Bacillus sphaericus*), zinc D-Ala-D-Ala carboxypeptidase (*Streptomyces albus*), vanY D-Ala-D-Ala carboxypeptidase (*Enterococcus faecium*), Ply118 L-Ala-D-Glu peptidase (bacteriophage A118), vanX D-Ala-D-Ala dipeptidase (*Enterococcus faecium*), pitrilysin (*Escherichia coli*), mitochondrial processing peptidase beta-subunit (*Saccharomyces cerevisiae*), eupitrilysin (*Homo sapiens*), leucyl aminopeptidase (*Bos taurus*), aminopeptidase I (*Saccharomyces cerevisiae*), membrane dipeptidase (*Homo sapiens*), glutamate carboxypeptidase (*Pseudomonas* sp.), peptidase T (*Escherichia coli*), Xaa-His dipeptidase (*Escherichia coli*), carboxypeptidase Ss1 (*Sulfolobus solfataricus*), O-sialoglycoprotein peptidase (*Mannheimia haemolytica*), beta-lytic metallopeptidase (*Achromobacter lyticus*), lysostaphin (*Staphylococcus simulans*), methionyl aminopeptidase 1 (*Escherichia coli*), aminopeptidase P (*Escherichia coli*), IgA1-specific metallopeptidase (*Streptococcus sanguinis*), tentoxilysin (*Clostridium tetani*), aminopeptidase S (*Streptomyces griseus*), glutamate carboxypeptidase II (*Homo sapiens*), IAP aminopeptidase (*Escherichia coli*), aminopeptidase Ap1 (*Vibrio proteolyticus*), aminopeptidase T (*Thermus aquaticus*), hyicolysin (*Staphylococcus hyicus*), carboxypeptidase Taq (*Thermus aquaticus*), anthrax lethal factor (*Bacillus anthracis*), deuterolysin (*Aspergillus flavus*), fungalysin (*Aspergillus fumigatus*), isoaspartyl dipeptidase (*Escherichia coli*), FtsH peptidase (*Escherichia coli*), glutamyl aminopeptidase (*Lactococcus lactis*), cytophagalysin (*Cytophaga* sp.), pappalysin-1 (*Homo sapiens*), pox virus metallopeptidase (vaccinia virus), Ste24 peptidase (*Saccharomyces cerevisiae*), HtpX peptidase (*Escherichia coli*), dipeptidyl-peptidase III (*Rattus norvegicus*), S2P peptidase (*Homo sapiens*), sporulation factor SpoIVFB (*Bacillus subtilis*), archaelysin (*Methanocaldococcus jannaschii*), D-aminopeptidase DppA (*Bacillus subtilis*), BlaR1 peptidase (*Staphylococcus aureus*), prtB g.p. (*Myxococcus xanthus*), enhancin (*Lymantria dispar* nucleopolyhedrovirus), glycyl aminopeptidase (*Sphingomonas capsulata*), IgA peptidase (*Clostridium ramosum*), StcE peptidase (*Escherichia coli*), Poh1 peptidase (*Saccharomyces cerevisiae*), JAMM-like protein (*Archaeoglobus fulgidus*), AMSH deubiquitinating peptidase (*Homo sapiens*), peptidyl-Asp metallopeptidase (*Pseudomonas aeruginosa*), camelysin (*Bacillus cereus*), murein endopeptidase (*Escherichia coli*), imelysin (*Pseudomonas aeruginosa*), Atp23 peptidase (*Homo sapiens*), tryptophanyl aminopeptidase 7-DMATS-type peptidase (*Aspergillus fumigatus*), ImmA peptidase (*Bacillus subtilis*), prenyl peptidase 2 (*Saccharomyces cerevisiae*), and Wss1 peptidase (*Saccharomyces cerevisiae*).

In an alternate embodiment, the protease may be an asparagine (N) protease/peptidase chosen from nodavirus peptidase (flock house virus), tetravirus coat protein (*Nudaurelia capensis* omega virus), Tsh-associated self-cleaving domain (*Escherichia coli*), picobirnavirus self-cleaving protein (Human picobirnavirus), YscU protein (*Yersinia pseudotuberculosis*), reovirus type 1 coat protein (Mammalian orthoreovirus 1), and poliovirus capsid VP0-type self-cleaving protein (human poliovirus 1).

In yet another embodiment, the protease may be a serine (S) protease/peptidase chosen from chymotrypsin A (*Bos taurus*), glutamyl peptidase I (*Staphylococcus aureus*), lysyl peptidase (*Achromobacter lyticus*), astrovirus serine peptidase (human astrovirus), togavirin (Sindbis virus), IgA1-specific serine peptidase (*Neisseria gonorrhoeae*), flavivirin (yellow fever virus), subtilisin Carlsberg (*Bacillus licheniformis*), kexin (*Saccharomyces cerevisiae*), prolyl oligopeptidase (*Sus scrofa*), dipeptidyl-peptidase IV (*Homo sapiens*), acylaminoacyl-peptidase (*Homo sapiens*), glutamyl peptidase (*Arabidopsis thaliana*), carboxypeptidase Y (*Saccharomyces cerevisiae*), D-Ala-D-Ala carboxypeptidase A (*Geobacillus stearothermophilus*), D-Ala-D-Ala carboxypeptidase B (*Streptomyces lividans*), D-Ala-D-Ala peptidase C (*Escherichia coli*), peptidase Clp (*Escherichia coli*), Xaa-Pro dipeptidyl-peptidase (*Lactococcus lactis*), Lon-A peptidase (*Escherichia coli*), cytomegalovirus assemblin (human herpesvirus 5), repressor LexA (*Escherichia coli*), signal peptidase I (*Escherichia coli*), signalase 21 kDa component (*Saccharomyces cerevisiae*), TraF peptidase (*Escherichia coli*), lysosomal Pro-Xaa carboxypeptidase (*Homo sapiens*), hepacivirin (hepatitis C virus), potyvirus P1 peptidase (plum pox virus), pestivirus NS3 polyprotein peptidase (bovine viral diarrhea virus 1), equine arteritis virus serine peptidase (equine arteritis virus), prolyl aminopeptidase (*Neisseria gonorrhoeae*), PS-10 peptidase (*Streptomyces lividans*), sobemovirus peptidase (cocksfoot mottle virus), luteovirus peptidase (potato leaf roll luteovirus), C-terminal processing peptidase-1 (*Escherichia coli*), tricorn core peptidase (*Thermoplasma acidophilum*), penicillin G acylase precursor (*Escherichia coli*), dipeptidyl-peptidase 7 (*Porphyromonas gingivalis*), HetR peptidase (*Anabaena variabilis*), signal peptide peptidase A (*Escherichia coli*), protein C (bacteriophage lambda), infectious pancreatic necrosis birnavirus Vp4 peptidase (infectious pancreatic necrosis virus), dipeptidase E (*Escherichia coli*), sedolisin (*Pseudomonas* sp. 101), rhomboid-1 (*Drosophila melanogaster*), SpoIVB peptidase (*Bacillus subtilis*), DmpA aminopeptidase (*Ochrobactrum anthropi*), nucleoporin 145 (*Homo sapiens*), lactoferrin (*Homo sapiens*), influenza A PA peptidase (influenza A virus), EGF-like module containing mucin-like hormone receptor-like 2 (*Homo sapiens*), Ssy5 peptidase (*Saccharomyces cerevisiae*), murein tetrapeptidase LD-carboxypeptidase (*Pseudomonas aeruginosa*), PIDD auto-processing protein unit 1 (*Homo sapiens*), Tellina virus 1 VP4 peptidase (Tellina virus 1), MUC1 self-cleaving mucin (*Homo sapiens*), dystroglycan (*Homo sapiens*), and gpO peptidase (Enterobacteria phage P2).

In a further embodiment, the protease may be a threonine (T) protease/peptidase chosen from archaean proteasome, beta component (*Thermoplasma acidophilum*), HsIV component of HsIUV peptidase (*Escherichia coli*), glycosylasparaginase precursor (*Homo sapiens*), gamma-glutamyltransferase 1 (*Escherichia coli*), ornithine acetyltransferase precursor (*Saccharomyces cerevisiae*), and polycystin-1 (*Homo sapiens*).

In still another embodiment, the protease may be a protease/peptidase of unknown catalytic type chosen from sporulation factor SpoIIGA (*Bacillus subtilis*), prohead peptidase (Enterobacteria phage T4), collagenase (*Porphyromonas gingivalis*), prohead peptidase (bacteriophage HK97), protein P5 murein endopeptidase (bacteriophage phi-6), Lit peptidase (*Escherichia coli*), homomultimeric peptidase (*Thermotoga maritima*), yabG protein (*Bacillus subtilis*), microcin-processing peptidase 1 (*Escherichia coli*), and AIDA-I self-cleaving autotransporter protein (*Escherichia coli*).

In a preferred embodiment, the protease may be a heat stable protease from *Bacillus*. In another preferred embodiment, the protease may be a broad spectrum protease from *Bacillus*. In an exemplary embodiment, the protease may be a heat stable, broad spectrum protease from *Bacillus licheniformis*. The strain of *B. licheniformis* may be PWD-1.

In some embodiments, the protease may be a naturally occurring protease, such that the naturally occurring protease may be isolated from its natural source. The isolated naturally occurring protease may be isolated as a biomass, partially purified, or purified to homogeneity from its natural source. In other embodiments, the protease may be a recombinant protein, wherein it is expressed in an organism other than its natural source. The recombinant protease may be essentially identical to the naturally occurring protease. Alternatively, the recombinant protease may be modified relative to the naturally occurring protease in that a particular amino acid residue(s) may be changed to other amino acid residue, or particular amino acid residues may be inserted or deleted. As above, the recombinant protease may be isolated as a biomass, partially purified, or completely purified from the organism that produces the recombinant protease. Methods for making recombinant proteins, as well as protein purification methods, are well known in the art. In a preferred embodiment, the protease may be within a biomass isolated from *Bacillus*.

The concentration of the protease or proteases in the supplement may range from about 1% to about 99.9% of the total weight of the supplement. The concentration may vary because the supplement may contain inert ingredients or excipients. In various embodiments, the concentration of the protease or proteases in the supplement may be about 1%, 2%, 3% 4%, 5%, 6%, 7%, 8%, 9%, 10%, 12%, 14%, 16%, 18%, 20%, 22%, 24%, 26%, 28%, 30%, 35%, 40%, 45%, 50%, 55%, 60%, 65%, 70%, 75%, 80%, 85%, 90%, 95%, or 99.9% of the total weight of the supplement.

(b) Inert Ingredients

In some embodiments, the supplement may contain at least one inert ingredient or excipient. Suitable excipients include diluents/fillers, binders, dispersion enhancers, lubricants, disintegrants, preservatives, buffering agents, pH modifying agents, flavoring agents, and coloring agents.

In one embodiment, the inert ingredient may be a filler or diluent. Non-limiting examples of suitable fillers or diluents include ground limestone (i.e., calcium carbonate), dibasic calcium phosphate (anhydrous or dihydrate), calcium phosphate tribasic, calcium silicate, di- or tri-basic calcium sulfate, clays (e.g., attapulgite, bentonite, kaolin, sepiolite), dolomite, gypsum, iron oxide, magnesium carbonate, magnesium oxide, magnesite, mica, perlite, talc, titanium minerals, vermiculite, zeolites, microcrystalline cellulose, cellulose derivatives, cellulose powder, cellulose esters (i.e., acetate and butyrate mixed esters), ethyl cellulose, methyl cellulose, hydroxypropyl cellulose, hydroxypropyl methylcellulose, polyvinylpyrrolidone, sodium carboxymethylcellulose, starch, modified starches, starch-lactose, starch-calcium carbonate, sodium starch glycolate, glucose, fructose, lactose, lactose monohydrate, sucrose, xylose, lacitol, mannitol, malitol, sorbitol, xylitol, maltodextrin, and trehalose.

In yet another embodiment, the inert excipient may be a dispersion enhancer. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In another embodiment, the excipient maybe a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, oligopeptides, and combinations thereof.

In a further embodiment, the inert ingredient may be a lubricant. Non-limiting examples of suitable lubricants include minerals such as talc or silica; and fats such as vegetable stearin, magnesium stearate, or stearic acid.

In a further embodiment, the excipient may be a disintegrant. Suitable examples of disintegrants include, but are not limited to, starches such as corn starch, potato starch, pregelatinized and modified starches thereof, sweeteners, clays, such as bentonite, microcrystalline cellulose, alginates, sodium starch glycolate, gums such as agar, guar, locust bean, karaya, pecitin, and tragacanth.

In still another embodiment, the inert excipient may be a buffering agent. Representative examples of suitable buffering agents include, but are not limited to, MOPS, HEPES, TAPS, Bicine, Tricine, TES, PIPES, MES, Tris buffers or buffered saline salts (e.g., Tris buffered saline or phosphate buffered saline). In another embodiment, the inert ingredient maybe a pH modifier. By way of non-limiting example, the pH modifying agent may be sodium carbonate, sodium bicarbonate, or citric acid.

In another alternate embodiment, the excipient may be a preservative. Non-limiting examples of suitable preservatives include antioxidants, such as alpha-tocopherol or ascorbate.

In yet another embodiment, the inert ingredient may be a flavoring agent. Suitable flavors include, but are not limited, to vegetable flavor, soybean flavor, herbal flavor, fruit flavor, fish flavor, milk flavor, and the like.

In still another embodiment, it may be desirable to include a coloring agent in the supplement. Suitable color additives include, but are not limited to, food, drug and cosmetic colors (FD&C), drug and cosmetic colors (D&C), or external drug and cosmetic colors (Ext. D&C).

The weight fraction of the inert excipient(s) in the supplement may be about 99% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the supplement.

(c) Dosage Forms

The supplement may be formulated in a variety of dosage forms. The dosage form may be solid or liquid. Typically, the supplement will be provided as a solid dosage form. Non-limiting examples of suitable dosage forms include dry powders, granules, pellets, grains, tablets, and the like.

(d) Preferred Supplement

In an exemplary embodiment, the supplement consists of a heat stable, broad spectrum protease from *Bacillus licheniformis*, ground limestone (i.e., calcium carbonate), and natural flavors. The heat stable, broad spectrum protease may be provided as a dried preparation (i.e., a biomass) of *Bacillus licheniformis*.

(II) Method for Decreasing a Population of Bacteria Comprising a *Clostridium* Species in the Upper Gastrointestinal Tract of a Subject Another aspect of the invention encompasses a method for decreasing a population of bacteria comprising a *Clostridium* species in the upper gastrointestinal tract of a subject. The method comprises administering to the subject a supplement consisting essentially of at least one protease in combination with a diet comprising a protein source that is digestible in the upper gastrointestinal tract and fermentable in the lower gastrointestinal tract of the subject, wherein the population of bacteria comprising a *Clostridium* species is reduced in the upper gastrointestinal tract of the subject.

Administration of the supplement consisting essentially of the protease(s) may improve the digestibility of dietary protein in the subject. Improved protein digestion results may reduce protein flow to the lower gastrointestinal tract. Reduced flow of dietary protein to the lower gastrointestinal tract may lead to reduced protein fermentation in the lower gastrointestinal tract. Consequently, *Clostridium* bacteria that normally reside in the lower intestinal tract may not increase in population and may not colonize the upper gastrointestinal tract. Upon administration of the supplement, therefore, the population of bacteria comprising *Clostridium* in the upper gastrointestinal tract of the subject may be reduced.

The term "upper gastrointestinal tract," as used herein, refers to the stomach and the duodenum of the small intestine. The term "lower gastrointestinal tract," as used herein, refers to the ileum of the small intestine and the cecum and colon of the large intestine.

(a) Administering the Supplement

The method comprises administering to the subject a supplement consisting of at least one protease. The supplement is detailed above in section (I).

The amount of protease(s) administered to the subject via the supplement can and will vary. In general, the concentration of the protease(s) administered to the subject may range from about 0.0001% to about 1% by weight of the subject's diet. In preferred embodiments, the concentration of the protease(s) administered to the subject may range from about 0.005% to about 0.5% by weight of the subject's diet. In various embodiments, the concentration of the protease(s) administered to the subject may be about 0.005%, 0.01%, 0.02%, 0.04%, 0.05%, 0.06%, 0.08%, 0.1%, 0.2%, 0.25%, 0.3%, 0.35%, 0.4%, 0.45%, or 0.5% by weight of the subject's diet. In an exemplary embodiment, the concentration of the protease(s) administered to the subject may be about 0.05% by weight of the subject's diet.

The duration of time the supplement is administered to the subject can and will vary. For example, the duration of time the supplement is administered to the subject may range from several days to several weeks, several months, or longer. In some embodiments, the supplement may be administered to the subject for the life of the subject.

(b) Protein Sources

A variety of protein sources may be included in the diet of the subject. A suitable protein source is one that is digestible in the upper gastrointestinal tract of the subject. That is, the protein source is able to be digested and absorbed in the upper intestinal tract of the subject. Furthermore, a suitable protein source is one that is fermentable in the lower gastrointestinal tract of the subject. Fermentation in the lower gastrointestinal tract refers to the process by which undigested proteins are digested by proteases and peptidases produced by bacteria and other microbes (e.g., methanogens) that reside in the lower gastrointestinal tract. The resultant digestion products are taken up by the resident bacteria and microbes, which may lead to increased populations of the bacteria and microbes in the lower gastrointestinal tract of the subject. Because of reverse peristalsis, bacteria and microbes from the lower gastrointestinal tract may be relocated to the upper gastrointestinal tract.

In general, the protein source may be an animal-derived protein, a plant-derived protein, or combinations thereof. In some embodiments, suitable sources of animal derived protein include blood meal, bone meal, fish meal, fish processing by-products, meat meal, meat and bone meal, poultry by-produce meal, and combinations thereof. In one embodiment, the animal-derived protein is not feather meal. Feather meal may be undigestible in some subjects (see Example 2). In other embodiments, suitable sources of plant-derived proteins include grains such as corn, oats, soybean, and the like; grain protein concentrates such as soy protein concentrate; legumes such as peas, lupine, alfalfa; distiller's grains; oilseed meals such as canola meal, cottonseed meal, flaxseed meal, soybean meal, sunflowerseed meal; and combinations thereof.

The amount of protein included in the diet of the subject can and will vary depending upon, for example, the type of subject and age of the subject. In general, the protein source may comprise from about 10% to about 30% by weight of the diet of the subject. In various embodiments, the amount of protein may be about 10%, 11%, 12%, 13%, 14%, 15%, 16%, 17%, 18%, 19%, 20%, 21%, 22%, 23%, 24%, 25%, 26%, 27%, 28%, 29%, or 30% by weight of the diet of the subject.

In general, administration of the supplement consisting essentially of the protease(s) improves the digestibility of dietary protein, provided the protein source is digestible in the upper gastrointestinal tract of the subject. The digestibility of dietary protein may be increased by about 1%, 2.5%, 5%, 7.5%, 10%, 12.5%, 15%, 17.5%, 20%, 25%, 30%, 35%, 40%, 45%, 50%, 60%, 70%, 80%, 90%, 100%, 150%, 200%, or more than 200%.

(c) Bacteria Comprising *Clostridium* Species

The method of the invention reduces the level of a population of bacteria comprising a *Clostridium* species in the upper gastrointestinal tract of the subject. The identity of the *Clostridium* species can and will vary. For example, the *Clostridium* species may be *C. botulinum, C. difficile, C. perfringens, C. spiroforme,* or *C. tetani*. In an exemplary embodiment, the species may be *C. perfringens*. The biotype of *C. perfringens* may be A, B, C, D, or E.

In general, the density of *Clostridium* bacteria in the upper gastrointestinal tract of the subject prior to administration of the supplement may range from about $10^2$ to about $10^7$ cfu/g. In various embodiments, the density of *Clostridium* bacteria in the upper gastrointestinal tract of subject prior to administration of the supplement may range from about $10^2$ to about $10^3$ cfu/g, from about $10^3$ to about $10^4$ cfu/g, from about $10^4$ to about $10^6$ cfu/g, from about $10^5$ to about $10^6$ cfu/g, or from about $10^6$ to about $10^7$ cfu/g.

After administration of the supplement, the population of bacteria comprising the *Clostridium* species typically is reduced in the upper gastrointestinal tract of the subject. For example, the density of the *Clostridium* species in the upper gastrointestinal tract of the subject may be reduced from about 0.5 log units to about 5 log units. In some embodiments, the density of the *Clostridium* species in the upper gastrointestinal tract may be decreased by about 0.5, 1, 1.5, 2, 2.5, 3, 3.5, 4, 4.5, or 5 log units. In other embodiments, the density of the *Clostridium* species in the upper gastrointestinal tract may be reduced by about 2%, 5%, 10%, 15%, 20%, 25%, 30%, 35%, 40%, 45%, 50%, 55%, 60%, 65%, 70%, 75%, 80%, 85%, 90%, 95%, or 99%.

The population of bacteria that is reduced in the upper gastrointestinal tract of the subject by administration of the supplement may further comprise species of bacteria other than *Clostridia*. For example, the population of bacteria may further comprise *Bacteriodes* spp., *Campylobacter* spp., *Citrobacter* spp., *Enterococcus* spp., *Escherichia* spp., *Fusobacterium* spp., *Hafnia* spp., *Klebsiella* spp., *Lactobacillis* spp., *Listeria* spp., and *Salmonella* spp., *Serratia* spp., and/or *Streptococcus* spp.

The density of the non-*Clostridium* bacteria may be reduced following administration of the supplement from about 0.5 log units to about 5 log units. In various embodiments, the density of the non-*Clostridium* bacteria in the upper gastrointestinal tract may be decreased by about 0.5, 1, 1.5, 2, 2.5, 3, 3.5, 4, 4.5, or 5 log units. In various other embodiment, the density of the non-*Clostridium* bacteria in the upper gastrointestinal tract may be reduced by about 2%, 5%, 10%, 15%, 20%, 25%, 30%, 35%, 40%, 45%, 50%, 55%, 60%, 65%, 70%, 75%, 80%, 85%, 90%, 95%, or 99%.

(d) Subjects

A variety of subjects may be administered the supplement that improves gut health. Suitable subjects include humans, food animals, companion animals, research animals, and zoo animals. Non-limiting examples of food animals include poultry (e.g., chickens, ducks, game hens, geese, guinea fowl/hens, quail, and turkeys), beef cattle, milk cows, veal, pigs, goats, sheep, and bison. Suitable companion animals include, but are not limited to, cats, dogs, horses, rabbits, rodents (e.g., mice, rats, hamsters, gerbils, and guinea pigs), hedgehogs, and ferrets. Examples of research animals include rodents, cats, dogs, rabbits, pigs, and non-human primates. Non-limiting examples of suitable zoo animals include non-human primates, lions, tigers, bears, elephants, giraffes, and the like.

In a preferred embodiment, the subject may be a chicken. The chicken may be a newborn chick, a starter chick, a grower chicken, a finisher chicken, a broiler chicken, a laying chicken, etc. The chicken may be housed in a cage, grown on litter, or may be free range.

In some embodiments, the subject may have elevated levels of bacteria comprising *Clostridium* in the upper gastrointestinal tract relative to a control subject. For example, the subject may have an increased level of bacteria comprising *Clostridium* because of a stimulated innate immune response, compromised digestive function, compromised gut barrier function, or combinations thereof. The control subject may be the same subject prior to changes in immune function, digestive function, etc. In other cases, the control subject may be a comparable healthy subject (i.e., same species, same sex, similar age, etc.) that does not have altered immune function, altered digestive function, etc.

In embodiments in which the subject has elevated levels of bacteria in the upper gastrointestinal tract, the immune system of the subject may be stimulated because of an underlying health condition. In one case, the subject may have a viral or parasitic infection. The viral or parasitic infection may be symptomatic (i.e., clinical) or asymptomatic (i.e., sub-clinical). In another case, the health condition may be due to a disease or disorder (e.g., an autoimmune disease such as diabetes, an inflammatory disorder such as arthritis, a cardiovascular condition, cancer, etc). Alternatively, the immune system of the subject may be stimulated because the subject is exposed to a stressful environment. The stressful environment may be due to exposure to environmental extremes (e.g., changes in temperature, etc.), crowded conditions, and the like. In another embodiment, digestive function and/or gut barrier function may be compromised because of the diet of the subject (e.g., the diet may be high (or low) in protein, high (or low) in fat, high (or low) in cereal grains, high (or low) in starch, etc.) or a change in the diet of the subject. Additionally, the intestinal system of the subject may be compromised because of inflammation of the mucosal cells lining the intestinal tract, a breech of the gut mucosal barrier (i.e., leaky tight junctions), altered mucosal cell function, altered mucosal cell structure, altered goblet cell function, altered intestinal motility, altered intestinal flora, or an imbalance of the intestinal flora.

A subject having elevated levels of bacteria comprising a *Clostridium* species in the upper gastrointestinal tract may be at risk for an intestinal disorder. Non-limiting examples of intestinal disorders caused by the growth or overgrowth of a *Clostridium* species include dysbacteriosis, diarrhea, necrotic enteritis, ulcerative enteritis, enterotoxicosis, and enterotoxemia. The intestinal disorder may be chronic, acute, clinical, or sub-clinical. In preferred embodiments, the intestinal disorder may be necrotic enteritis. Accordingly, after administration of the supplement, the subject may be less susceptible to the intestinal disorders listed above.

After administration of the supplement, the subject may have a reduced level of alpha-1-glycoprotein relative to the level of alpha-1-glycoprotein in that subject prior to administration of the supplement or relative to the level of alpha-1-glycoprotein in a comparable subject not administered the supplement. Levels of alpha-1-glycoprotein are typically used an indirect measurement of inflammation. The levels of alpha-1-glycoprotein may be reduced by about 5%, 10%, 15%, 20%, 25%, 30%, 35%, 40%, 45%, 50%, 55%, 60%, 65%, 70%, or more than 70%.

Additionally, the subject administered the supplement may have improved gut barrier function relative to prior to administration of the supplement or relative to a comparable subject not administered the supplement. Improved gut barrier function may be due to the regeneration of mucosal villi or microvilli or the reinstatement of impermeable tight junctions. Moreover, the subject administered the supplement may have improved performance data. For example, the subject administered the supplement may have increased weight gain, improved feed to gain ratio, improved performance indices, etc. relative to a subject not administered the supplement.

In still another embodiment, the subject may be in need of treatment with the supplement because the subject has an intestinal disorder or has an increased risk for developing an intestinal disorder, defined above. As used herein, the terms "treatment" or "treating" refer to preventing the onset or development of an intestinal disorder; slowing, inhibiting, or reversing the progression of am intestinal disorder; or preventing, inhibiting, or alleviating the symptoms of an intestinal disorder. Accordingly, the subject in need of treatment may have an increased population of bacteria comprising *Clostridium* in the upper gastrointestinal tract relative, a stimulated innate immune response, compromised digestive function, compromised gut barrier function, or combinations thereof. Administration of the supplement, therefore, generally treats or prevents the intestinal disorder.

(e) Exemplary Embodiment

In an exemplary embodiment, the subject is a chicken and the supplement comprises a *Bacillus* biomass containing a broad spectrum protease. The diet of the chicken may comprise one or more plant-based proteins, optionally cereal grains, and optionally an animal-based protein. The level of protein in the diet of the chicken may range from about 12% to about 25% by weight of the diet of the chicken. Administration of the supplement to the chicken generally reduces the level of *Clostridium perfringens* in the upper gastrointestinal tract of the chicken, and reduces the susceptibility of the chicken to necrotic enteritis.

(f) Administering Additional Optional Agents

In some embodiments, the method may further comprise administering at least one additional agent to the subject. Suitable agents that may be administered to the subject include antibiotic or antimicrobial agents, antioxidants, amino acids, organic acids, vitamins, and minerals. Agents that are excluded from being administered to the subject in conjunction with the supplement include other enzymes (e.g., starch hydrolyzing carbohydrases, non-starch hydrolyzing carbohydrases, lipases, nucleases, and lipases) and inner salts of quaternary amine carboxylic acids (e.g., betaine and similar compounds).

In one embodiment, the additional agent may be an antibiotic agent. Suitable antibiotic agents include aminoglycosides such as amikacin, gentamicin, kanamycin, neomycin, netilmicin, streptomycin, and tobramycin); a carbecephem such as loracarbef; carbapenems such as certapenem, imipenem, and meropenem; cephalosporins such as cefadroxil cefazolin, cephalexin, cefaclor, cefamandole, cephalexin, cefoxitin, cefprozil, cefuroxime, cefixime, cefdinir, cefditoren, cefoperazone, cefotaxime, cefpodoxime, ceftazidime, ceftibuten, ceftizoxime, and ceftriaxone; macrolides such as azithromycin, clarithromycin, dirithromycin, erythromycin, and troleandomycin; monobactam; penicillins such as amoxicillin, ampicillin, carbenicillin, cloxacillin, dicloxacillin, nafcillin, oxacillin, penicillin G, penicillin V, piperacillin, and ticarcillin; polypeptides such as bacitracin, colistin, and polymyxin B; quinolones such as ciprofloxacin, enoxacin, gatifloxacin, levofloxacin, lomefloxacin, moxifloxacin, norfloxacin, ofloxacin, and trovafloxacin; sulfonamides such as mafenide, sulfacetamide, sulfamethizole, sulfasalazine, sulfisoxazole, and trimethoprim-sulfamethoxazole; and tetracyclines such as demeclocycline, doxycycline, minocycline, and oxytetracycline). In another embodiment, the additional agent may be an antimicrobial agent such as ketoconazole, amoxicillin, cephalexin, miconazole, econazole, acyclovir, and nelfinavir.

In still another embodiment, the additional agent may be an antioxidant. Non-limiting examples of appropriate antioxidants include ascorbic acid and its derivatives, N-acetylcysteine, benzyl isothiocyanate, berberine, boswellic acid, caffeic acid, canthaxantin, carnosic acid, carotenoids (e.g., alpha-carotene, beta-carotene, lycopene, lutein, asaxanthin, cryptoxanthin, zeaxanthin), carnosol, carvacrol, catechins, celery seed extract, chlorogenic acid, citric acid and its derivatives, clove extract, cocoa flavonols, coffee bean extract, curcumin, devils claw root, 3,4-dihydroxybenzoic acid, diosgenin, diosmetin, edetic acid, ellagic acid, esculetin, esculin, eucalyptus extract, eugenol, ferulic acid, flavonoids (e.g., catechin, epicatechin, epicatechin gallate, epigallocatechin (EGO), epigallocatechin gallate (EGCG), and polyphenol epigallocatechin-3-gallate), flavones (e.g., apigenin, chrysin, luteolin), flavonols (e.g., datiscetin, myricetin, daemfero), flavanones, fraxetin, fumaric acid, gallic acid and its derivatives, gentian extract, glabridin, gluconic acid, glutathione-R, glutathione-O, glycine, grape seed extract, green tea or extract thereof, gum guaiacum, hesperetin, honokiol, 4-hydroxycinammic acid (i.e., p-coumaric acid), hydroxyglutaric acid, N-hydroxysuccinic acid, hydroxytryrosol, isoflavones (e.g., diadzein, glycitein, and genistein), lactic acid and its derivatives, lecithin and its derivatives, licorice extract, ligustilide, alpha-lipoic acid, magnolol, malic acid, maltol, nordihydroguaiaretic acid (NDGA), oxalic acid, phosphatidylcholine, phytic acid, pimento extract, pomegranate extract, pycnogenol, quercetin, resveratrol, rice bran extract, rosemary extract, rosmarinic acid, sage extract, sesamol, silymarin, sinapic acid, succinic acid, syringic acid, tartaric acid, thymol, thymoquinone, tocopherols (i.e., alpha-, beta-, gamma- and delta-tocopherol), tocotrienols (i.e., alpha-, beta-, gamma- and delta-tocotrienols), tryptanthrin, tyrosol, vanillic acid, tryptamine, tyramine, uric acid, ursolic acid, vitamin K and its derivatives, vitamin/coenzyme Q10, wheat germ oil, and combinations thereof.

In yet another embodiment, the additional agent may be an amino acid. The amino acid may be a standard amino acid or derivative thereof (i.e., one of the 20 amino acids encoded by the genetic code, as well as selenocysteine, methionine-hydroxy analog, and pyrrolysine), a non-standard amino acid or derivative thereof (e.g., 2-aminoisobutyric acid, beta-alanine, carnitine, citrulline, dehydroalanine, gamma-aminobutyric acid, homocysteine, lanthionine, ornitinine, etc.), branched-chain amino acids, or combinations thereof.

In another embodiment, the additional agent may be an organic acid or salt thereof. Suitable organic acids include mono-, di-, or tri-carboxylic acids comprising from two to about twenty-five carbon atoms. Non-limiting examples of suitable carboxylic acids include formic acid, acetic acid, propionic acid, butanoic acid, benzoic acid, lactic acid, malic acid, tartaric acid, mandelic acid, citric acid, fumaric acid, sorbic acid, succinic acid, adipic acid, glycolic acid, and glutaric acid.

In an alternate embodiment, the additional agent may be a vitamin. Suitable vitamins include vitamin A (retinol), vitamin B1 (thiamine), vitamin B2 (riboflavin), vitamin B3 (niacin), vitamin B5 (pantothenic acid), vitamin B6 (pyridoxine), vitamin B7 (biotin), vitamin B9 (folic acid), vitamin B12 (cobalamins), vitamin C (ascorbic acid), vitamin D (calciferol), vitamin E (tocopherol), vitamin K (phylloquinone/phytol naphthoquinone), and combinations thereof.

In a further embodiment, the additional agent may be a mineral. Non-limiting examples of suitable minerals include calcium, chromium, copper, iodine, iron, magnesium, manganese, molybdenum, phosphorus, potassium, selenium, and zinc. Suitable forms of any of the foregoing minerals include soluble mineral salts, slightly soluble mineral salts, insoluble mineral salts, chelated minerals, mineral complexes, non-reactive minerals such as carbonyl minerals, reduced minerals, and combinations thereof.

(III) Method for Reducing Protein to the Lower Gastrointestinal Tract of a Subject A further aspect of the invention encompasses a method for reducing protein flow to the lower intestinal tract of a subject. The method comprises administering to the subject a supplement consisting essentially of at least one protease in combination with a diet comprising a protein source that is digestible in the upper gastrointestinal tract and fermentable in the lower gastrointestinal tract of the subject, wherein reduction of protein flow to the lower gastrointestinal tract decrease a population of bacteria comprising a *Clostridium* species in the upper gastrointestinal tract of the subject.

The supplement consisting essentially of the protease(s) is described above in section (I). Administration of the supplement, protein sources, bacterial species, and subjects are detail above in section (II).

EXAMPLES

The following examples are included to demonstrate various embodiments of the invention. It should be appreciated by those of skill in the art that the techniques disclosed in the examples represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth is to be interpreted as illustrative and not in a limiting sense.

Examples 1-4

Experimental models for producing NE generally have drawn from field experience linking its occurrence to coccidiosis challenge, diets containing a high content of poorly digestible non-starch polysaccharides (NSP) found in cereal grains, and diets containing fishmeal and animal protein. Models for inducing NE in chickens generally include a multiday challenge with actively replicating *C. perfringens* (Cp). The following examples were designed to exclude Cp challenge so that factors that trigger the growth of Cp, which are already present in the hindgut of day old chicks, could be analyzed. Thus, by studying subclinical enteritis, it may be possible to elucidate factors that can tip the balance of the relationship between microbiota and host to either positively or negatively impact overall gut health.

Example 1

Effect of NSP Enzymes on Gut Health in Broilers Fed a Rye-Wheat Diet

The objective of the following example was to study the effects of several feed additive treatments to improve gut health in chickens fed a diet containing rye and wheat as a cereal source and exposed to a coccidiosis challenge.

The diet was a 22% crude protein (CP), 1.21%/1.07% total/digestible lysine mash diet containing 33% rye, 25% wheat, and 31% soybean meal. The feed additives were none (control), an antibiotic (bacitracin methylene disalicylate (BMD); 60 ppm) and an NSP enzyme mixture containing xylanase, glucanase, and glycosidase (sold under the tradename CIBENZA™ CSM by Novus International, Inc.; 500 mg/kg). Half of each group was challenged (on day 0) with cycling Eimeria as a 3× overdose of a 3-species live oocyst vaccine (available under ADVENT® from Viridus Animal Health, LLC). Body weights were taken on days 14, 21, and 28; Cp counts were taken on days 14 and 21; digesta viscosity was measured on day 28; and intestinal morphology was visualized on days 15 and 22.

Figure 2:
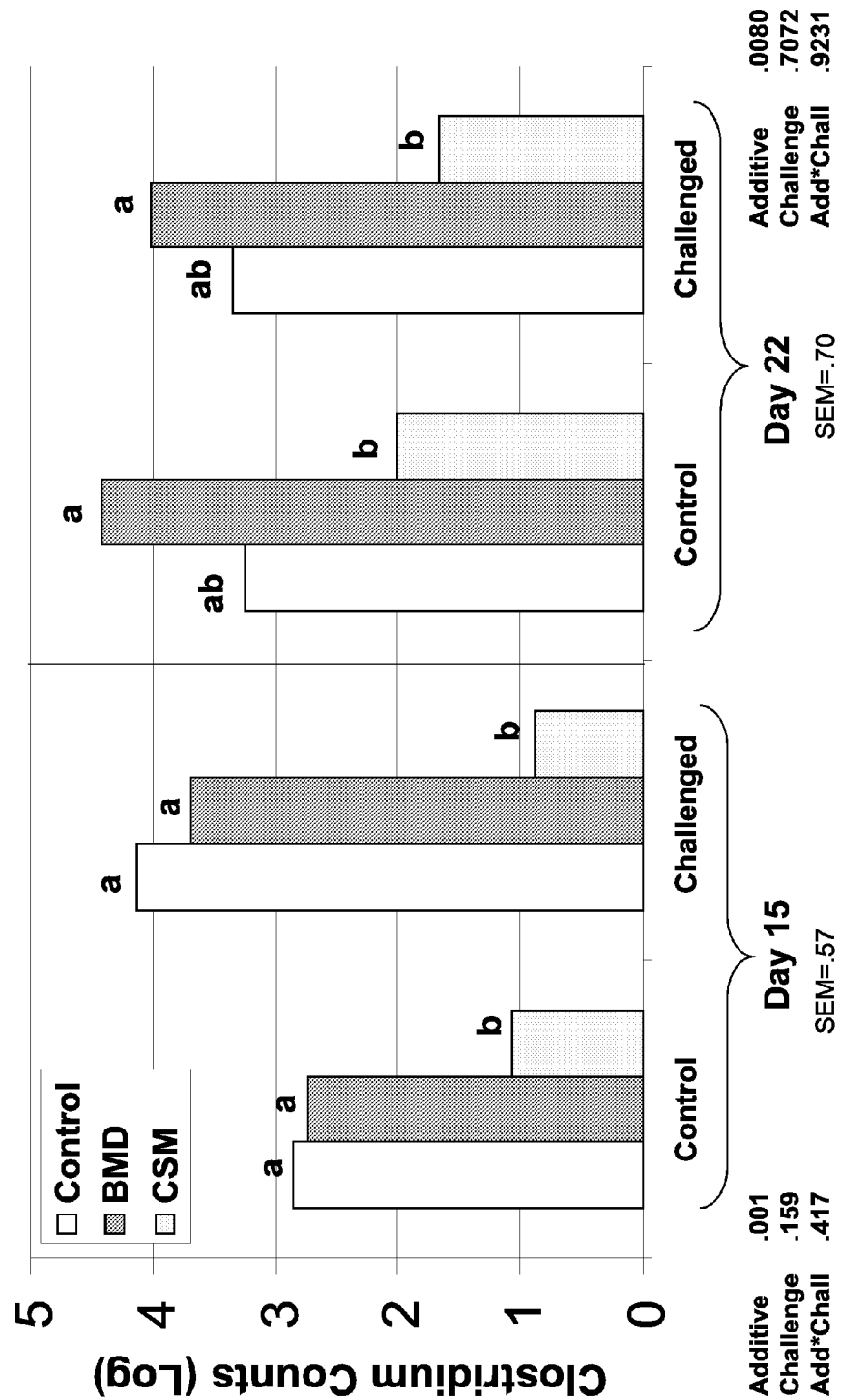
FIG. 2 shows the reduction of Clostridial counts in the lower intestinal tract of broilers treated with NSP enzymes irrespective of coccidiosis challenge. Plotted is the $\log_{10}$ of Clostridial counts in each group at day 15 and day 22. Broilers were fed a rye-wheat diet. Treatment groups were: no additive (control)±challenge, antibiotic (DMP)±challenge, and NSP enzymes (CSM)±challenge (a,b; $P<0.01$).

Although the overdose of coccidiosis in this high viscosity diet resulted in a 4-5% reduction ($P<0.01$) in the efficiency of gain, there were no interactions with any of the feed additive effects. Therefore, the results are presented as main effects averaged across coccidiosis challenge. Addition of feed additives improved the 28 day Performance Index [(period gain× period livability)/period feed efficiency; PI] from 145 for control to 188 and 284 for the antibiotic and NSP enzymes, respectively (FIG. 1; $P<0.01$). The PI improvement was consistent throughout the trial (i.e., from days 14-28) for the NSP enzymes and was also associated with a significant reduction in digesta viscosity ($P<0.01$). In contrast, the antibiotic improved PI only at day 28 and had no effect on digesta viscosity. The NSP enzymes were also associated with a 1.5 to 2.5 log unit reduction in cultured Cp from the hindgut and lower ileum (FIG. 2; $P<0.01$), irrespective of challenge. The antibiotic did not have a significant effect on Cp number, however. Overall livability for the trial was in excess of 95%; there were no treatment-related differences and no *Clostridium*-related deaths.

Intestinal morphology at days 15 and 22 of the study was used to assess intestinal health with respect to the various feed additive treatments. Overdose of coccidiosis vaccine affected intestinal morphology negatively, showing significantly reduced mucosa development, reduced villus height, and higher (poorer) crypt/villus ratios in the duodenum and mid-small intestine at both days relative to non-challenged controls. These negative effects, which are consistent with local inflammatory responses, were more pronounced in the mid-small intestine for challenged birds in the absence of NSP enzymes on day 15, however. Ileal morphology was not significantly affected at either day by any additive or coccidial challenge. Addition of NSP enzymes improved intestinal (duodenum and mid-small intestine) morphology as represented by reduced crypt/villus ratio, indicating that at least a portion of the improved performance was related to improved gut health and reduced demands on the crypt stem cell proliferation.

These results indicate that subjecting broilers to this challenge of dietary NSP-containing ingredients created intestinal inflammation and stimulated Cp growth in the lower intestinal tract. Moreover, addition of NSP enzymes improved performance, mitigated intestinal inflammation, and reduced Cp overgrowth.

Example 2

Effect of Enzymes on Gut Health in Broilers Fed a Diet Containing Rye-Wheat as the Cereal Source and Feather Meal as the Protein Source

In the following example, the diet was modified to assess the impact of an animal protein source that is less well digested than soybean meal when fed from 1 to 21 days of age. The diet was 23.5% CP, 1.38%/1.21% total/digestible lysine mash diet containing 38% rye, 25% wheat, 20% soybean meal, and 7% feather meal. The birds were challenged on day 0 with a 3× overdose of the live oocyst coccidiosis vaccine essentially as detailed above in Example 1. The feed additive treatments were none (control), NSP enzymes (see Example 1), and a protease (i.e., CIBENZA™ DP100, which is a dried preparation of *B. licheniformis* comprising a heat stable protease; 500 mg/kg). Body weights were taken on days 14, 21, and 28; Cp counts were taken on day 15; digesta viscosity was measured on day 21, and intestinal morphology was assessed on day 8.

Figure 3:
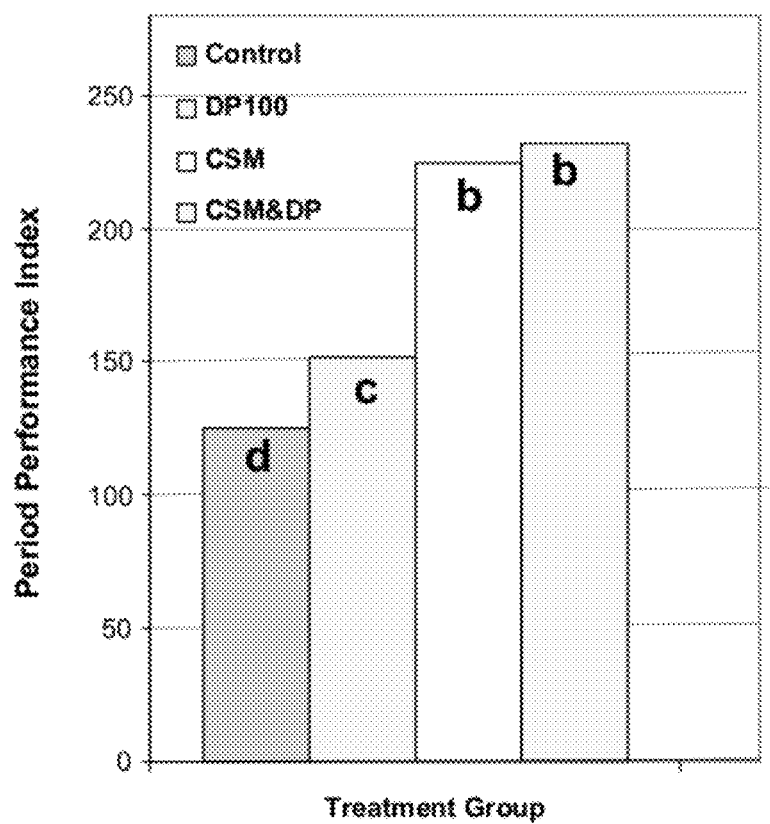
FIG. 3 presents the performance index on day 22 for each treatment group. Broilers were fed a rye-wheat and feather meal diet. Treatment groups were: no additive (control), protease (DP100), NSP enzymes (CSM), and a combination of protease and NSP enzymes (CSM&DP) (a,b,c,d; $P<0.01$). Analysis: CSM: $P=0.001$; DP100: $P=0.634$; CSM*DP100: $P=0.428$; SEM=1.099.
Figure 4:
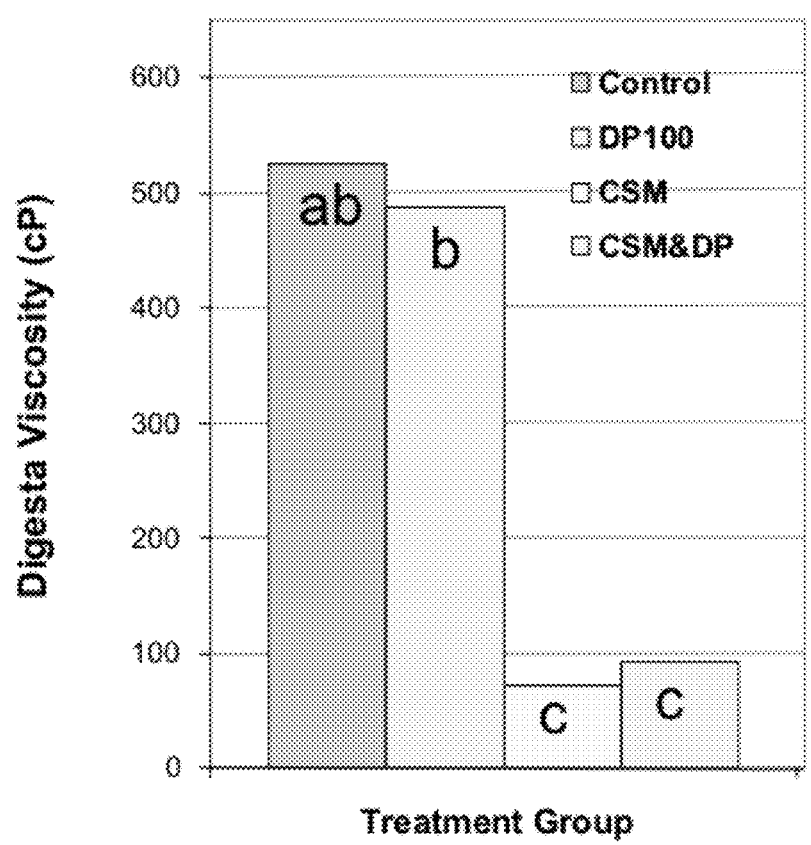
FIG. 4 illustrates the reduction of digesta viscosity by NSP enzymes in broilers fed a rye-wheat and feather meal diet. Treatment groups were: no additive (control), protease (DP100), NSP enzymes (CSM), and a combination of protease and NSP enzymes (CSM&DP) (a,b,c; $P<0.01$). Analysis: CSM: $P=0.001$; DP100: $P=0.071$; CSM*DP100: $P=0.046$; SEM=49.1.
Figure 5:
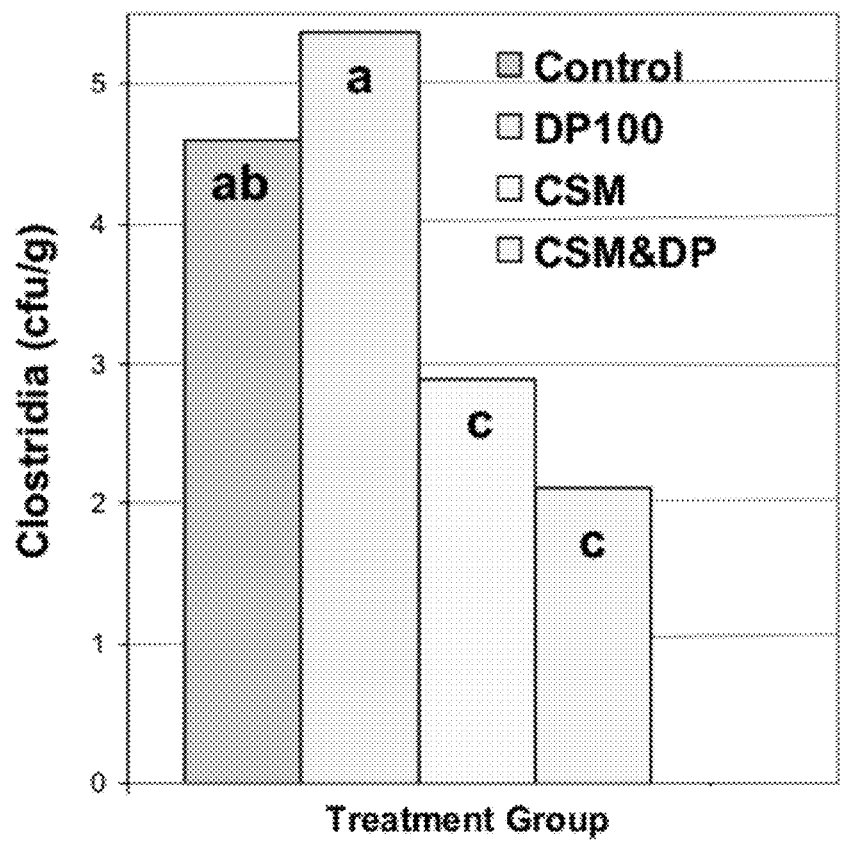
FIG. 5 presents Clostridial counts (log units) on day 15 in the lower ileum of broilers fed a rye-wheat and feather meal diet. Treatment groups were: no additive (control), protease (DP100), NSP enzymes (CSM), and a combination of protease and NSP enzymes (CSM&DP) (a,b,c; $P<0.01$). Analysis: CSM: $P=0.001$; DP100: $P=0.895$; CSM*DP100: $P=0.038$; SEM=1.099.

The performance index (PI) was improved by addition of the NSP enzymes and modestly improved by the protease (FIG. 3; $P<0.01$). The combination of the two enzyme additives did not result in a further PI improvement. Digestive viscosity was reduced most by the NSP enzymes (FIG. 4; $P<0.01$), and Cp numbers in the lower ileum were reduced by 1.5-2 log units by the NSP enzymes (FIG. 5; $P<0.01$).

In summary, while the addition of the NSP enzymes to this high feather meal diet reduced ileal concentrations of Cp, there was no evidence that addition of the protease to this diet had any similar inhibitory impact on Cp growth. It seems likely that feather meal is not digestible in the upper intestinal tract and addition of the protease did not increase its digestibility (which is evidence by the high digesta viscosity in the presence of the protease).

Example 3

Effect of Protease on Gut Health in Broilers Fed a Rye-Wheat Diet and an Optional Animal Protein Source In the following example, birds were fed one of two different diets. On diet contained a normal protein level and no animal protein; it was formulated to 22% CP and 1.38%/1.21% total/digestible lysine and contained 20% rye, 25% wheat, 32% soybean meal, and 13% corn. The second diet contained 14% poultry by-product meal (PBM) and was formulated to provide an excess of CP (30%) and total/digestible lysine of 1.65%/1.38% (the +PBM diet also contained 20% rye, 25% wheat, 32% soybean meal, and 5% corn). The diets of half of each group were supplemented with the protease (essentially as detailed above in Example 2). All of the birds were challenged with a 3× overdose of the live oocyst coccidiosis vaccine essentially as detailed above in Example 1, except that the challenge was received on day 7 of the 28 day trial. Body weights were recorded on days 14, 21, and 21; and Cp counts were taken on day 15.

Figure 6:
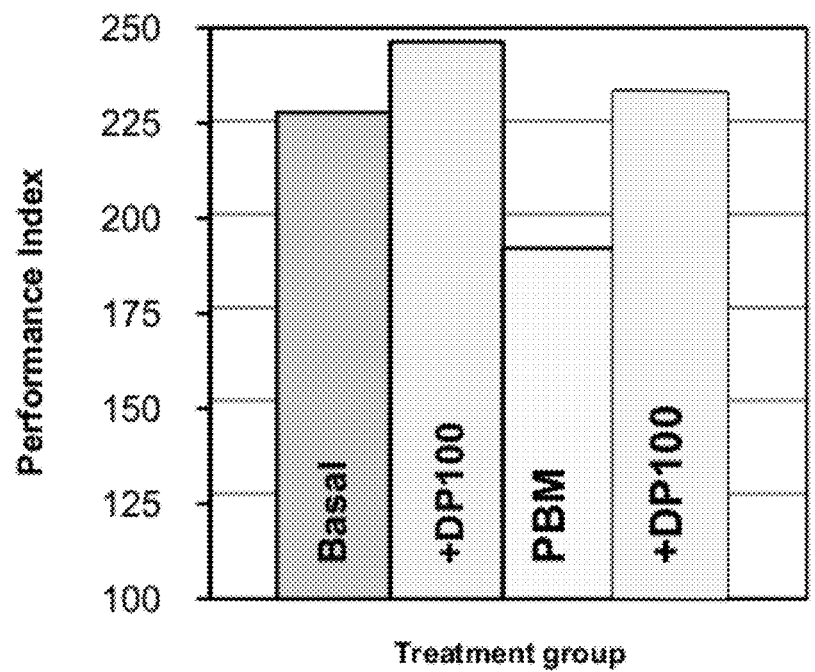
FIG. 6 shows the performance index effect of broilers fed two different diets. The basal diet contained 22% crude protein. The high protein diet contained 30% crude protein by supplementation with 14% poultry by-product meal (PBM). Treatments were no protease and protease (+DP100).
Figure 7:
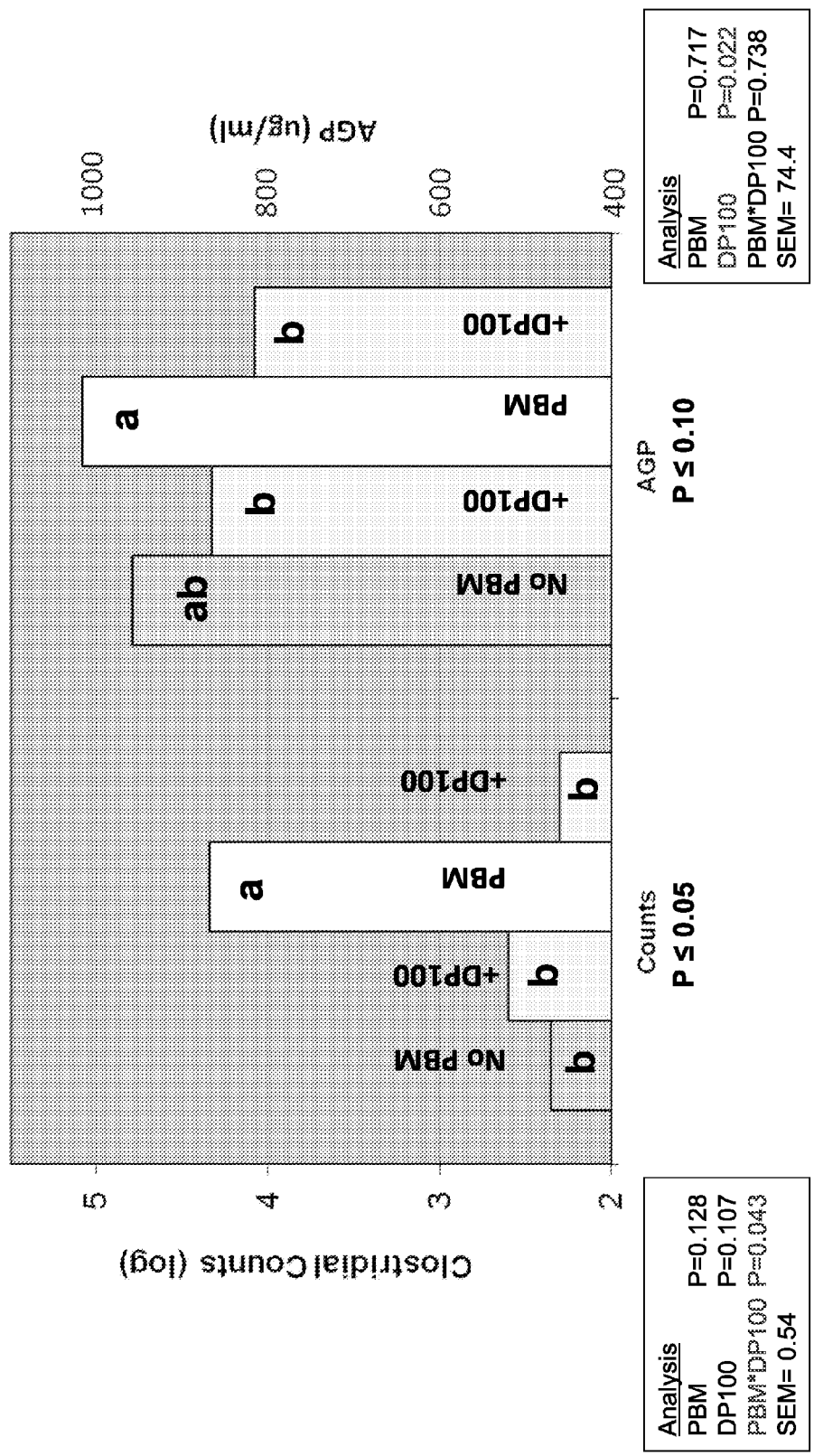
FIG. 7 presents Clostridial counts (left) and serum levels of alpha1-acid glycoprotein (AGP) (right) for each treatment group. The basal diet contained 22% crude protein. The high protein diet contained 30% crude protein by supplementation with 14% poultry by-product meal (PBM). Treatments were no protease and protease (+DP100) (a,b; $P<0.10$).

The 28-day results indicated a reduction in PI with the high protein +PBM diet. The addition of the protease to this high protein diet, however, maintained PI at a level comparable to that of the normal protein diet (FIG. 6). While these results were not significant, they are directionally consistent with the notion that excess protein in the hindgut facilitates bacterial overgrowth and, consequently, a negative influence on performance. Ileal concentrations of Cp were increased approximately 2 log units in birds with the high protein PBM diet (FIG. 7; P<0.01). Addition of the protease to the high protein +PBM diet resulted in a 2 log unit reduction in Cp levels that were similar to the normal protein diet (FIG. 7). The acute phase protein, alpha1-acid glycoprotein (AGP), was measured in the serum on day 15 as an indicator of intestinal barrier function. Addition of the protease to either diet resulted in reductions of serum AGP levels (FIG. 7; P<0.1) regardless of dietary protein level. The protease, therefore, improved intestinal barrier function.

These results suggest that minimizing the flow of digestible protein to the hindgut in the face of subclinical enteritis reduced Cp levels in the gut. Reducing the flow of digestible protein could be accomplished by reducing the intake of dietary protein or by supplementing the diet with a protease. The protease increases digestibility of the dietary protein in the upper intestinal tract and, as a consequence, minimizes protein flow to the hindgut.

Example 4

Effect of Protease on Performance of Broilers Fed a Corn-Soybean Meal Diet with Different Levels of Protein The following example was designed to test whether the dietary protease could be used to replace some of the protein in a standard diet. Standard starter (0-14 days), grower (14-28 days), and finisher (28-42 days) diets were formulated to reflect industry standards. The standard diets were modified to contain 7.5% less CP and amino acids (the −7.5% CP diet) or 10% less CP and amino acids (the −10% CP diet) by reducing the amount of soybean meal and increasing the amount of corn accordingly. One half of each diet group was supplemented with the protease (essentially as described in Example 2). This example differed from the previous three examples in that no coccidoisis challenge was given.

Figure 8:
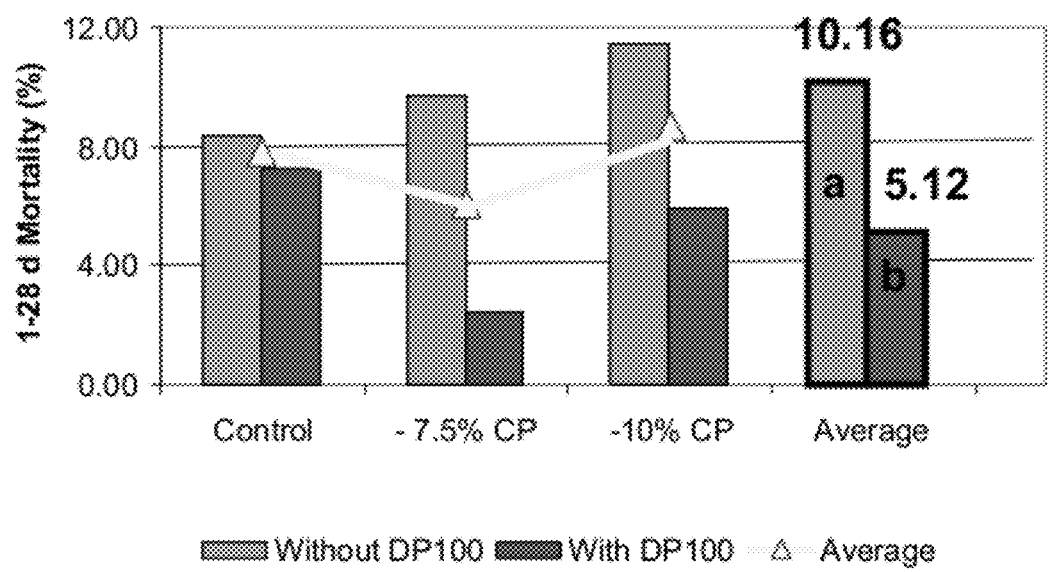
FIG. 8 illustrates that protease reduced mortality due to a spontaneous necrotic enteritis outbreak. The broilers were fed a standard corn-soybean diet (control), a corn-soybean diet with 7.5% less crude protein (−7.5% CP), or a corn-soybean diet with 10% less CP (−10% CP). Treatments were no protease and protease.

As expected, reducing the amount of protein in the diet had negative effects on body weight, PI, etc. relative to those receiving the standard diet. The addition of the protease increased body weight and PI of the animals receiving the reduced protein diets, but never to control levels (data not shown). During days 14-28 of the study, however, there was an outbreak of necrotic enteritis. It was discovered that the groups receiving the supplemental protease had reduced mortality, irrespective of diet. As shown in FIG. 8, protease significantly reduced mortality by about 50% in each group (P<0.02). The reduction of mortality was particularly striking in the groups fed the reduced protein diets.

What is claimed is:

1. A method for decreasing a population of bacteria comprising *Clostridium perfringens* in the upper gastrointestinal tract of a subject irrespective of coccidiosis challenge, the method comprising administering to the subject a supplement consisting essentially of at least one protease in combination with a diet comprising a protein source that is digestible in the upper gastrointestinal tract and fermentable in the lower gastrointestinal tract of the subject, wherein the population of bacteria comprising *Clostridium perfringens* is reduced in the upper gastrointestinal tract of the subject, irrespective of coccidiosis challenge, and mortality due to necrotic enteritis is reduced by about 50%, and wherein the protease is a serine protease that is administered in an amount from about 0.005% to about 0.5% by weight of the diet and the subject is poultry.

2. The method of claim 1, wherein the subject has an increased Performance Index (PI), when PI is measured by (period gain×period livability)/period feed efficiency.

* * * * *